(12) United States Patent
NarasimhaMurthy et al.

(10) Patent No.: US 12,287,320 B2
(45) Date of Patent: Apr. 29, 2025

(54) METHODS AND APPARATUS FOR HASHING AND RETRIEVAL OF TRAINING IMAGES USED IN HILN DETERMINATIONS OF SPECIMENS IN AUTOMATED DIAGNOSTIC ANALYSIS SYSTEMS

(71) Applicant: Siemens Healthcare Diagnostics Inc., Tarrytown, NY (US)

(72) Inventors: Venkatesh NarasimhaMurthy, Hillsborough, NJ (US); Vivek Singh, Princeton, NJ (US); Yao-Jen Chang, Princeton, NJ (US); Benjamin S. Pollack, Jersey City, NJ (US); Ankur Kapoor, Plainsboro, NJ (US); Rayal Raj Prasad Nalam Venkat, Princeton, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/755,467

(22) PCT Filed: Oct. 22, 2020

(86) PCT No.: PCT/US2020/056922
§ 371 (c)(1),
(2) Date: Apr. 29, 2022

(87) PCT Pub. No.: WO2021/086721
PCT Pub. Date: May 6, 2021

(65) Prior Publication Data
US 2024/0168006 A1 May 23, 2024

Related U.S. Application Data

(60) Provisional application No. 62/929,066, filed on Oct. 31, 2019.

(51) Int. Cl.
*G01N 33/49* (2006.01)
*G06F 18/2431* (2023.01)
(Continued)

(52) U.S. Cl.
CPC ....... *G01N 33/491* (2013.01); *G06F 18/2431* (2023.01); *G06T 7/0016* (2013.01);
(Continued)

(58) Field of Classification Search
CPC ...... G01N 33/49; G01N 33/491; G01N 35/04; G01N 2035/0406; G06T 7/00;
(Continued)

(56) References Cited

U.S. PATENT DOCUMENTS 9,739,783 B1 8/2017 Kumar et al.
10,198,832 B2 2/2019 De Fauw et al.
(Continued)

FOREIGN PATENT DOCUMENTS

CN 105825509 A 8/2016
CN 106372390 A 2/2017
(Continued)

OTHER PUBLICATIONS

Extended EP Search Report dated Dec. 8, 2022 of corresponding European Application No. 20883271.7, 4 Pages.
(Continued)

*Primary Examiner* — Tuan H Nguyen

(57) ABSTRACT

A method of characterizing a specimen to be analyzed in an automated diagnostic analysis system provides an HILN classification (hemolysis, icterus, lipemia, normal) of the specimen along with a basis for that determination. The method includes assigning a hash code to each training image of a sample specimen used in the characterization training process. In response to an HILN determination for a test specimen, the method can retrieve via the hash code
(Continued)

one or more of the closest matching training images upon which the HILN classification is based. The one or more of the closest matching training images can be displayed alongside of the one or more images of the test specimen. Quality check modules and systems configured to carry out the method are also described, as are other aspects.

20 Claims, 6 Drawing Sheets

(51) Int. Cl.
*G06T 7/00* (2017.01)
*G06T 7/10* (2017.01)
*G16H 10/40* (2018.01)
*G16H 50/20* (2018.01)
*G01N 35/04* (2006.01)

(52) U.S. Cl.
CPC ............... *G06T 7/10* (2017.01); *G16H 10/40* (2018.01); *G16H 50/20* (2018.01); *G01N 2035/0406* (2013.01); *G06T 2207/10024* (2013.01); *G06T 2207/20081* (2013.01); *G06T 2207/20084* (2013.01); *G06T 2207/30024* (2013.01)

(58) Field of Classification Search
CPC ............ G06T 7/0016; G06T 7/10; G06T 2207/10024; G06T 2207/20081; G06T 2207/20084; G06T 2207/30024; G16H 10/40; G16H 50/20; G06F 18/2431
See application file for complete search history.

(56) References Cited

U.S. PATENT DOCUMENTS

| | | | |
|---|---|---|---|
| 2012/0140230 A1 | 6/2012 | Miller | |
| 2012/0250984 A1* | 10/2012 | Taylor | G06V 20/52 382/173 |
| 2017/0364771 A1 | 12/2017 | Pinheiro et al. | |
| 2017/0372193 A1 | 12/2017 | Mailhe et al. | |
| 2018/0045654 A1 | 2/2018 | Park et al. | |
| 2018/0372648 A1 | 12/2018 | Wissmann et al. | |
| 2019/0041318 A1 | 2/2019 | Wissmann et al. | |
| 2019/0079083 A1* | 3/2019 | Harwanegg | G01N 33/54346 |
| 2019/0271714 A1 | 9/2019 | Kluckner et al. | |
| 2019/0277870 A1* | 9/2019 | Kluckner | G06T 7/11 |
| 2020/0151498 A1 | 5/2020 | Sun et al. | |
| 2020/0158745 A1 | 5/2020 | Tian et al. | |
| 2021/0064927 A1 | 3/2021 | Kluckner et al. | |
| 2021/0133971 A1 | 5/2021 | Ma et al. | |
| 2021/0164965 A1 | 6/2021 | Ma et al. | |
| 2021/0334972 A1 | 10/2021 | NarasimhaMurthy et al. | |

FOREIGN PATENT DOCUMENTS

| | | |
|---|---|---|
| CN | 106408562 A | 2/2017 |
| CN | 108596166 A | 9/2018 |
| EP | 3018482 A1 | 5/2016 |
| JP | 2009-512009 A | 3/2009 |
| JP | 2013-117860 A | 6/2013 |
| JP | 2019500100 A | 1/2019 |
| JP | 2019531783 A | 11/2019 |
| JP | 2020-519853 A | 7/2020 |
| WO | 2017102827 A1 | 6/2017 |
| WO | 2017106645 A1 | 6/2017 |
| WO | 2017132168 A1 | 8/2017 |
| WO | 2017132169 A1 | 8/2017 |
| WO | 2018009405 A1 | 1/2018 |
| WO | 2018039380 A1 | 3/2018 |
| WO | 2018081617 A1 | 5/2018 |
| WO | 2018105062 A1 | 6/2018 |
| WO | 2018/191287 A1 | 10/2018 |

OTHER PUBLICATIONS

Jiang Menglin et al: "Joint Kernel-Based Supervised Hashing for Scalable Histopathological Image Analysis", Nov. 18, 2015 (Nov. 18, 2015), 16th European Conference—Computer Vision—ECCV 2020, Cornell University Library, 201 Olin Library Cornell University Ithaca, NY 14853, pp. 366-373, XP047565145.

PCT International Search Report and Written Opinion dated Jan. 21, 2021 (16 Pages).

Goodfellow, Ian, et al. "Generative adversarial nets", Advances in neural information processing systems 27. 2014. pp. 1-9.

Hideki, Aso et al. "Deep Representation Learning by Multi-Layer Neural Networks"; The Japanese Society for Artificial Intelligence; Year: Jul. 2013, vol. 28 No. 4, pp. 649-659.

Huang, Gao, et al. "Densely connected convolutional networks", Proceedings of the IEEE conference on computer vision and pattern recognition. 2017. pp. 4700-4708.

Jégou, Simon, et al. "The one hundred layers tiramisu: Fully convolutional densenets for semantic segmentation." Proceedings of the IEEE conference on computer vision and pattern recognition workshops. 2017.

Lecun, Yann et al. "Gradient-based learning applied to document recognition" Proceedings of the IEEE, New York, US, vol. 86, No. 11, Nov. 1, 1998, pp. 2278-2323, 1998 // ISSN: 0018-9219, DOI: 10. 1109/5.726791.

Ren, Shaoqing et al.: "Faster R-CNN: Towards Real-Time Object Detection with Region Proposal Networks"; IEEE Transactions on Pattern Analysis and Machine Intelligence; vol. 39, No. 6, Sep. 13, 2015; pp. 1137-1149; XP055473561; USA; ISSN:0162-8828; DOI: 10.1109/TPAMI.2016.2577031.

Shah Urmil et al: "A Review of Deep Learning Models for Computer Vision", 2018 IEEE Punecon, IEEE, Nov. 30, 2018 (Nov. 30, 2018), pp. 1-6, XP033568970, DOI: 10.1109/PUNECON.2018. 8745417.

* cited by examiner

METHODS AND APPARATUS FOR HASHING AND RETRIEVAL OF TRAINING IMAGES USED IN HILN DETERMINATIONS OF SPECIMENS IN AUTOMATED DIAGNOSTIC ANALYSIS SYSTEMS

CROSS REFERENCE TO RELATED APPLICATION APPLICATIONS

This disclosure is a 371 national stage application for PCT/US2020/056917, filed Oct. 22, 2020, which claims priority to, and the benefit of, U.S. Provisional Patent Application No. 62/929,066, entitled "METHODS AND APPARATUS FOR HASHING AND RETRIEVAL OF TRAINING IMAGES USED IN AN HILN DETERMINATION OF A SPECIMEN IN AN AUTOMATED DIAGNOSTIC ANALYSIS SYSTEM," filed Oct. 31, 2019, the disclosures of which are hereby incorporated by reference in their entireties for all purposes herein.

FIELD

This disclosure relates to methods and apparatus configured to characterize a specimen in an automated diagnostic analysis system.

BACKGROUND

Automated diagnostic analysis systems may analyze a specimen, such as, e.g., urine, blood serum, blood plasma, interstitial liquid, cerebrospinal liquid, and the like, to identify an analyte or other constituent contained in the specimen. Such specimens are usually contained within specimen containers (e.g., specimen collection tubes) and are transported via automated tracks to various, pre-processing, pre-screening including imaging, and analyzers within an automated diagnostic analysis system.

A specimen may be pre-screened, pre-processed with one or more reagents and possibly other materials added therein, and then analyzed at one or more analyzers. Analytical measurements may be performed on the specimen via fluorometric absorption readings by using a beam of interrogating radiation and taking fluorescent readings, or by taking luminescent readings, or the like. The analytical measurements allow determination of an amount of an analyte or other constituent contained in the specimen using well-known techniques.

However, the presence of an interferent (e.g., hemolysis, icterus, and/or lipemia) in the specimen, which may result from a patient condition or sample pre-processing, may adversely affect test results of the analyte or constituent measurement obtained from one or more analyzers. For example, the presence of hemolysis (H) in the specimen, which may be unrelated to a patient's disease state, may cause a different interpretation of the disease condition of the patient. Similarly, the presence of icterus (I) and/or lipemia (L) in the specimen may also cause a different interpretation of the disease condition of the patient.

A pre-screening process for determining a presence of, and in some cases a degree of, an interferent, such as H, I, and/or L, in a specimen to be analyzed may thus be performed in an automated diagnostic analysis system. This pre-screening process involves automated detection of H, I, and/or L, or normal (N) based on one or more images of the specimen captured at one or more imaging stations of the automated diagnostic analysis system. The pre-screening process may perform an HILN (hemolysis, icterus, and/or lipemia, or normal) determination on the captured image; that is, the pre-screening process may determine a presence of, and optionally, a degree or index for H, I, and/or L in a specimen, or it may determine that the specimen is normal (N) and thus can proceed to be further analyzed by one or more analyzers.

However, in some instances, the pre-processing to determine HILN may not be correct. Accordingly, there is an unmet need to provide methods and apparatus for improving an HILN determination in an automated diagnostic analysis system.

SUMMARY

According to a first aspect, a method of characterizing a specimen in an automated diagnostic analysis system is provided. The method includes receiving a plurality of training images for training an HILN (hemolytic, icteric, lipemic, normal) network of a quality check module comprising a computer in the automated diagnostic analysis system, each of the training images depicting a sample specimen in a specimen container, and assigning a hash code to each of the training images via a hashing network of the HILN network. The method also includes receiving one or more images of a specimen in a specimen container to be analyzed in the automated diagnostic analysis system; characterizing the specimen to be analyzed based on the received one or more images via the HILN network using the plurality of training images to determine a classification index comprising hemolytic, icteric, lipemic, or normal classes; and retrieving via the hash code one or more of the plurality of training images upon which the determined classification index of the characterized specimen is based.

According to another aspect, a method of characterizing a specimen is provided. The method includes receiving a plurality of training images to train an HILN network, each of the training images depicting a sample specimen in a specimen container; assigning a hash code to each of the training images via a hashing network; receiving one or more images of a specimen in a specimen container to be analyzed by the HILN network; characterizing the specimen to be analyzed based on the received one or more images via the HILN network using the plurality of training images to determine a classification index of a hemolytic, icteric, lipemic, or normal class; and retrieving via the hash code of one or more of the plurality of training images upon which the classification index is based.

According to yet another aspect, a quality check module of an automated diagnostic analysis system is provided. The quality check module includes a plurality of image capture devices arranged around an imaging location configured to capture multiple images from multiple viewpoints of a specimen container containing a specimen therein, and a computer coupled to the plurality of image capture devices. The computer is configured and operative via programming instructions to input a first plurality of images captured by the plurality of image capture devices to an HILN (Hemolytic, Icteric, Lipemic, Normal) network executing on the computer, the first plurality of images representing a plurality of training images for training the HILN network, each of the training images depicting a sample specimen in a specimen container. The computer is also configured and operative via programming instructions to assign a hash code to each of the training images via a hashing network of the HILN network, and input one or more second images captured by the plurality of image capture devices to the HILN network executing on the computer, wherein the one or more second images represent a same specimen in a specimen container to be analyzed in the automated diagnostic analysis system. The computer is further configured and operative via programming instructions to characterize the specimen to be analyzed based on the one or more second images via the HILN network using the plurality of training images to determine a classification index comprising hemolytic, icteric, lipemic, and normal classes; and retrieve via the hash code one or more of the plurality of training images upon which the determined classification index of the characterized specimen is based.

Still other aspects, features, and advantages of this disclosure may be readily apparent from the following description and illustration of a number of example embodiments, including the best mode contemplated for carrying out the invention. This disclosure may also be capable of other and different embodiments, and its several details may be modified in various respects, all without departing from the scope of the disclosure. This disclosure is intended to cover all modifications, equivalents, and alternatives falling within the scope of the claims.

BRIEF DESCRIPTION OF THE DRAWINGS

The drawings, described below, are for illustrative purposes and are not necessarily drawn to scale. Accordingly, the drawings and descriptions are to be regarded as illustrative in nature, and not as restrictive. The drawings are not intended to limit the scope of the disclosure in any way.

DETAILED DESCRIPTION

Figure 1:
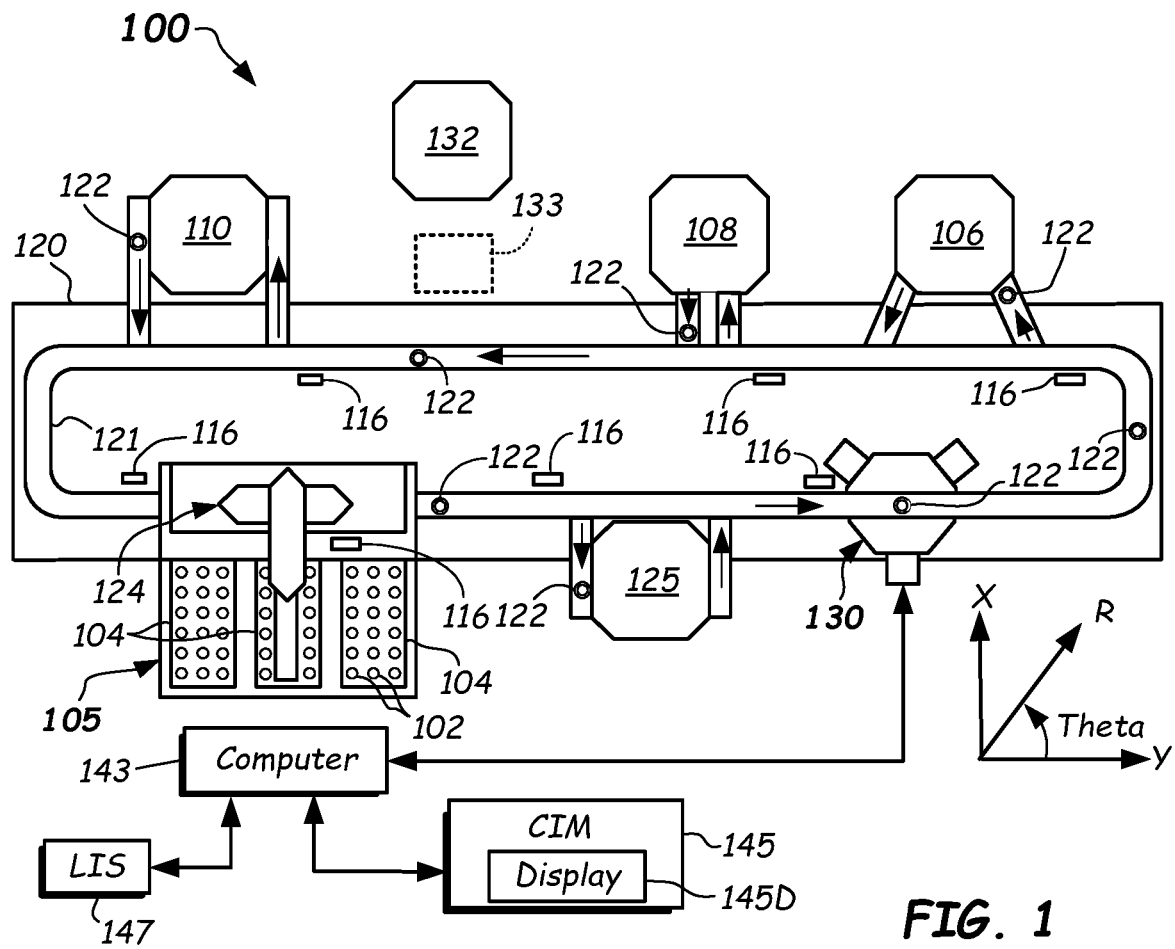
FIG. 1 illustrates a top schematic view of an automated diagnostic analysis system including one or more quality check modules configured to carry out HILN determination methods according to one or more embodiments.

An incorrect HILN determination may be difficult to debug, because little if any information is known to be provided explaining how the pre-screening process has determined each HILN result. Embodiments provided herein may facilitate debugging of an incorrect HILN determination that has taken place in an automated diagnostic analysis system.

Pre-screening of a specimen (e.g., blood serum or plasma specimen) contained in a specimen container may be performed at a quality check module of an automated diagnostic analysis system to determine the presence of and, in some embodiments, the degree (index) of an interferent in a serum or plasma portion of the blood specimen. Checking the quality of the specimen at the quality check module via imaging allows specimens that are not acceptable to avoid being routed to an analyzer, which may produce an errant result and further may waste valuable analyzer time. An output of the pre-screening process may be an HILN index, which indicates the presence of one or more of hemolysis (H), icterus (I), or lipemia (L) in the serum or plasma portion of the specimen, or a determination of being normal (N), which indicates that a serum or plasma portion may include acceptably low amounts of H, I, and L, or none at all. Hemolysis may be defined as a condition in the serum or plasma portion wherein red blood cells are destroyed during pre-processing, which leads to the release of hemoglobin from the red blood cells into the serum or plasma portion such that the serum or plasma portion takes on a reddish hue. The degree of hemolysis may be quantified by assigning a hemolytic index. Icterus may be defined as a condition of the blood where the serum or plasma portion is discolored dark yellow, which may be caused by an accumulation of bile pigment (bilirubin). The degree of icterus may be quantified by assigning an icteric index. Lipemia may be defined as a presence in the blood of an abnormally-high concentration of emulsified fat, such that the serum or plasma portion has a whitish or milky appearance. The degree of lipemia may be quantified by assigning a lipemic index.

A pre-screening process may determine just a presence of HIL or a degree or sub-class (index) of H (e.g., H0-H6 in some embodiments and more or less in other embodiments), a degree or sub-class (index) of I (e.g., I0-I6 in some embodiments and more or less in other embodiments), and/or a degree or sub-class (index) of L (e.g., L0-L4 in some embodiments and more or less in other embodiments). In some embodiments, the pre-screening process may include determination of an un-centrifuged (U) class for a serum or plasma portion of a specimen that has not been centrifuged or that has been improperly centrifuged.

In addition, the pre-screening process may classify (or "segment") various regions of the specimen container and specimen, so as to identify regions of the image corresponding to, for example, a serum or plasma portion, a settled blood portion, a gel separator (if used), air, a label or labels, and/or specimen container cap. A specimen container holder and/or background may also be classified. As a result of the segmentation, the type of specimen container (e.g., via obtained height and/or width (diameter)), and/or type and/or color of a specimen container cap can be determined.

A quality check module of an automated diagnostic analysis system configured to execute a pre-screening characterization method may include an HILN network, such as, e.g., a segmentation convolutional neural network (SCNN), that receives as input one or more images of a sample specimen taken at an imaging station (e.g., imaging station of a quality check module) of the automated diagnostic analysis system (described in more detail below). An SCNN may include, in some embodiments, greater than 100 operational layers including, e.g., BatchNorm, ReLU activation, convolution (e.g., 2D), dropout, and deconvolution (e.g., 2D) layers to extract features, such as simple edges, texture, and parts of the serum or plasma portion and label-containing regions. Top layers, such as fully convolutional layers, may be used to provide correlation between parts. The output of the layer may be fed to a SoftMax layer, which produces an output on a per pixel (or per superpixel (patch)—including n×n pixels) basis concerning whether each pixel or patch is classified as HIL or N. In some embodiments, only an output of HIL or N may be provided by the SCNN. In other embodiments, the output of the SCNN may include multiple subclasses (indexes) of HIL, such as greater than 20 classes of HIL, so that for each interferent present, an estimate of the interferent level (index) of the interferent is also obtained. In some embodiments, the SCNN may also include a front-end container segmentation network (CSN) to determine a container type and a container boundary. In some embodiments, the segmentation convolutional neural network (SCNN) may comprise a deep semantic segmentation network (DSSN) or other deep learning convolutional neural network. Alternatively, other types of HILN networks may be used.

Should the specimen be found to contain one or more of H, I, and L, a suitable notice may be provided to the operator, and/or the specimen container may be taken off line (1) to perform a remediation to rectify the one or more of the H, I, or L, (2) to redraw the specimen, or (3) to perform other processing. Thus, the ability to pre-screen for HILN before analysis by one or more analyzers may advantageously (a) minimize time wasted analyzing specimens that are not of the proper quality for analysis, (b) avoid or minimize erroneous test results, (c) minimize patient test result delay, and/or (d) avoid wasting of patient specimen.

However, in some instances, an HILN determination for one or more specimens may not be correct. Such an incorrect HILN determination may likely be caused by an insufficient number and/or scope of sample specimen images (training images) used to train the HILN network. To facilitate debugging of an incorrect HILN determination, characterization methods and quality check modules configured to carry out the pre-screening process in accordance with one or more embodiments herein assign a hash code to each training image used to train the HILN network. The hash code assigned in training can index and be later used to facilitate rapid retrieval of the training image or images, upon which the HILN determination was based, using a hashing table or the like. Further, characterization methods and quality check modules can provide for retrieval, via the hash code, of one or more of the training images upon which an HILN determination of a characterized specimen in an automated diagnostic analysis system is based. This allows an image or images of the test sample specimen with an incorrect HILN determination to be compared to the specific training image or images upon which the incorrect HILN determination is based. The image or images of the test sample specimen with the incorrect HILN determination and the image or images of the training specimen upon which the HILN determination was based can be displayed on a display screen, such as by a side-by-side for comparison. As appropriate, additional training images based on the incorrectly-characterized sample specimen may then be included in the HILN network, for example, through retraining, to improve the performance thereof. Other corrective measures may also, or alternatively, be taken based on the retrieved training images. Furthermore, in some embodiments, a pre-screening process may assign to each HILN determination of a test sample, a predictive confidence level (of the determination's accuracy) based on the output of the classification network (e.g., SCNN), thus alerting system operator to suspect the (i.e., through low confidence value) HILN determination, and possibly flag such determination for retraining.

Further details of inventive characterization methods, quality check modules configured to carry out the inventive characterization methods, and automated diagnostic analysis systems including one or more quality check modules will be further described with reference to FIGS. 1-7 herein.

Figure 2:
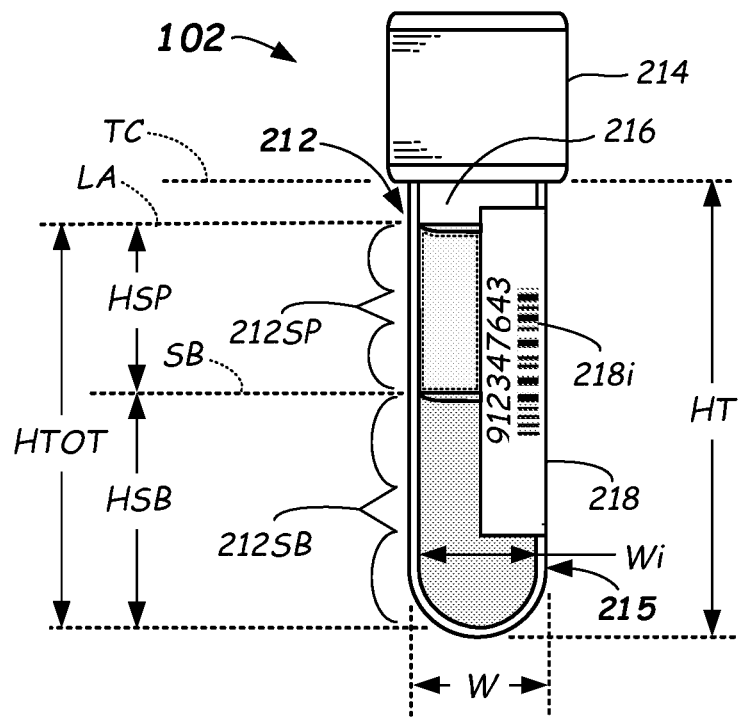
FIG. 2 illustrates a side plan view of a specimen container including a separated specimen with a serum or plasma portion that may contain an interferent.

FIG. 1 illustrates an automated diagnostic analysis system 100 capable of automatically processing multiple specimen containers 102 containing sample specimens 212 (see FIG. 2). The specimen containers 102 may be provided in one or more racks 104 at a loading area 105 prior to transportation to, and analysis by, one or more analyzers (e.g., first analyzer 106, second analyzer 108, and/or third analyzer 110) arranged about the automated diagnostic analysis system 100. More or less numbers of analyzers may be in the system 100. The analyzers may be any number or combination of clinical chemistry analyzers, assaying instruments, and/or the like. The specimen containers 102 may be any suitably transparent or translucent container, such as a blood collection tube, test tube, sample cup, cuvette, or other clear or opaque glass or plastic container capable of containing and allowing imaging of the specimen 212 contained therein. The specimen containers 102 may be varied in size and type.

Specimens 212 (see FIG. 2) may be provided to the automated diagnostic analysis system 100 in the specimen containers 102, which may be capped with a cap 214. The caps 214 may be of different types and/or colors (e.g., red, royal blue, light blue, green, grey, tan, yellow, or color combinations), which may have meaning in terms of what test the specimen container 102 is used for, the type of additive included therein, whether the container includes a gel separator, vacuum capability, or the like. Other colors may be used. In one embodiment, the cap color and/or cap type may be determined by the characterization method described herein.

Each of the specimen containers 102 may be provided with a label 218, which may include identification information 218i (i.e., indicia) thereon, such as a barcode, alphabetic characters, numeric characters, or combinations thereof. The identification information 218i may be machine readable at various locations about the automated diagnostic analysis system 100. The machine readable information may be darker (e.g., black) than the label material (e.g., white material) so that it can be readily imaged. The identification information 218i may indicate, or may otherwise be correlated, via a Laboratory Information System (LIS) 147 or other test order database, to a patient's identification as well as tests to be performed on the specimen 212. The identification information 218i may indicate other or additional information. Such identification information 218i may be provided on the label 218, which may be adhered to or otherwise provided on an outside surface of the tube 215. As shown in FIG. 2, the label 218 may not extend all the way around the specimen container 102 or all along a length of the specimen container 102 such that from the particular front viewpoint shown, a large part of a serum or plasma portion 212SP is viewable (the part shown dotted) and unobstructed by the label 218. However, as will be apparent, the specimen 212 can be viewable and imaged from multiple viewpoints and thus images can be captured from the multiple viewpoints so that at least one viewpoint will have the serum or plasma portion 212SP being viewable.

The specimen 212 may include the serum or plasma portion 212SP and a settled blood portion 212SB contained within the tube 215. Air 216 may be provided above the serum and plasma portion 212SP and a liquid-air line of demarcation between the air 216 and the serum and plasma portion 212SP is defined as the liquid-air interface (LA). The line of demarcation between the serum or plasma portion 212SP and the settled blood portion 212SB is defined as a serum-blood interface (SB). An interface between the air 216 and cap 214 is defined as a tube-cap interface (TC). The height of the tube (HT) is defined as a height from a bottom-most part of the tube 215 to a bottom of the cap 214, and may be used for determining tube size. A height of the serum or plasma portion 212SP is HSP and is defined as a height from a top of the serum or plasma portion 212SP to a top of the settled blood portion 212SB. A height of the settled blood portion 212SB is HSB and is defined as a height from the bottom of the settled blood portion 212SB to a top of the settled blood portion 212SB at SB. HTOT is a total height of the specimen 212 and equals HSP plus HSB.

Figure 3:
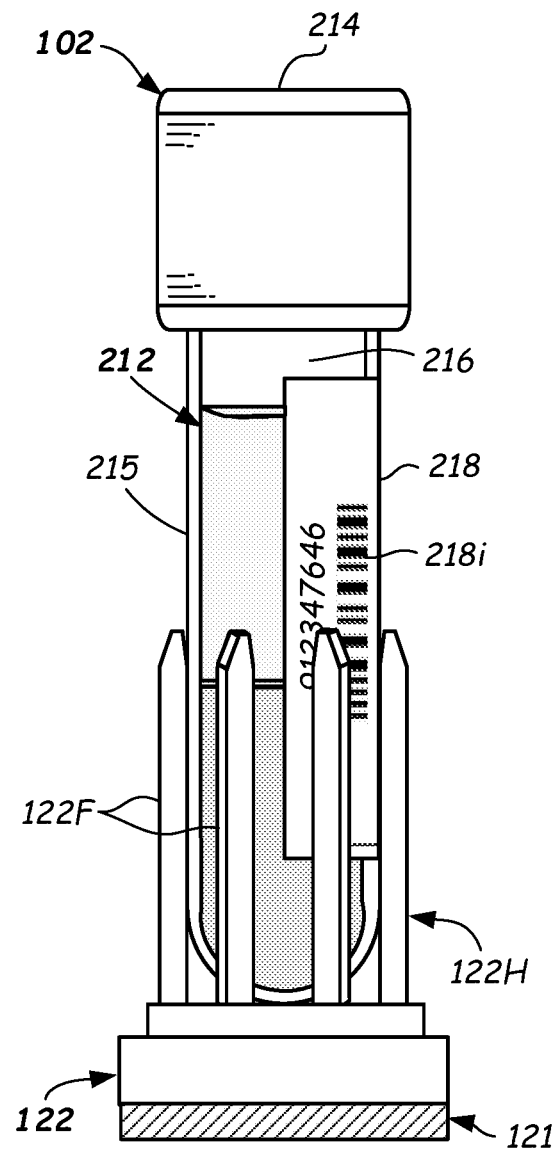
FIG. 3 illustrates a side plan view of the specimen container of FIG. 2 held in an upright orientation in a holder that can be transported by a carrier within the automated diagnostic analysis system of FIG. 1, and which can facilitate imaging.

In more detail, automated diagnostic analysis system 100 may include a base 120 (FIG. 1) (e.g., a frame, floor, or other structure) upon which a track 121 may be mounted. The track 121 may be a railed track (e.g., a mono rail or a multiple rail), a collection of conveyor belts, conveyor chains, moveable platforms, or any other suitable type of conveyance mechanism. Track 121 may be circular or any other suitable shape and may be a closed track (e.g., endless track) in some embodiments. Track 121 may, in operation, transport individual ones of the specimen containers 102 to various locations spaced about the track 121 as held in carriers 122 (FIG. 3).

Carriers 122 may be passive, non-motored pucks that may be configured to carry a single specimen container 102 on the track 121, or optionally, an automated carrier including an onboard drive motor, such as a linear motor that is programmed to move about the track 121 and stop at pre-programmed locations. Other configurations of carrier 122 may be used. Carriers 122 may each include a holder 122H (see FIG. 3) configured to hold the specimen container 102 in a defined upright position and orientation. The holder 122H may include a plurality of fingers (or leaf springs) 122F (a few labeled) that secure the specimen container 102 on the carrier 122, but some may be moveable or flexible to accommodate different sizes (e.g., diameters) of the specimen containers 102. In some embodiments, carriers 122 may leave from the loading area 105 after being offloaded from the one or more racks 104. The loading area 105 may serve a dual function of also allowing reloading of the specimen containers 102 from the carriers 122 to the loading area 105 after pre-screening and/or analysis by one or more analyzers 106-110 is complete.

A robot 124 may be provided at the loading area 105 and may be configured to grasp the specimen containers 102 from the one or more racks 104 and load the specimen containers 102 onto the carriers 122, such as onto an input lane of the track 121. Robot 124 may also be configured to reload specimen containers 102 from the carriers 122 to the one or more racks 104. The robot 124 may include one or more (e.g., at least two) robot arms or components capable of X (lateral) and Z (vertical—out of the page, as shown), Y and Z, X, Y, and Z, or r (radial) and theta (rotational) motion. Robot 124 may be a gantry robot, an articulated robot, an R-theta robot, or other suitable robot wherein the robot 124 may be equipped with robotic gripper fingers oriented, sized, and configured to pick up and place the specimen containers 102.

Upon being loaded onto track 121, the specimen containers 102 carried by carriers 122 may progress to a first pre-processing station 125. For example, the first pre-processing station 125 may be an automated centrifuge configured to carry out fractionation of the specimen 212 into the serum or plasma portion 212SP and settled blood portion 212SB. Carriers 122 carrying specimen containers 102 may be diverted to the first pre-processing station 125 by inflow lane or other suitable robot. After being centrifuged, the specimen containers 102 may exit on an outflow lane, or otherwise be removed by a robot, and continue along the track 121. In the depicted embodiment, the specimen container 102 in carrier 122 may next be transported to a quality check module 130 that is configured to carry out pre-screening and methods of characterizing a specimen according to embodiments of the disclosure, as will be further described herein.

The quality check module 130 is configured to pre-screen and carry out the characterization methods described herein to automatically determine a presence of, and optionally an extent or degree of H, I, and/or L contained in a specimen 212, or whether the specimen is normal (N). If found to contain effectively-low amounts of H, I and/or L, so as to be considered normal (N), the specimen 212 may continue on the track 121 and then may be analyzed by the one or more analyzers (e.g., first, second, and/or third analyzers 106, 108, and/or 110). Thereafter, the specimen container 102 may be returned to the loading area 105 for reloading to the one or more racks 104.

In some embodiments, in addition to an HILN determination, segmentation of the specimen container 102 and specimen 212 may take place. From the segmentation data, post processing by computer 143 may be used for quantification of the specimen 212 (i.e., determination of HSP, HSB, HTOT, and determination of location of SB or SG, and LA). In some embodiments, characterization of the physical attributes (e.g., size—height and/or width/diameter) of the specimen container 102 may also take place at the quality check module 130. Such characterization may include determining HT and W, and possibly TC, and/or W or Wi. From this characterization, the size of the specimen container 102 may be extracted. Moreover, in some embodiments, the quality check module 130 may also determine cap color and/or cap type, which may be used as a safety check and may catch whether a wrong tube type has been used for the test ordered.

In some embodiments, a remote station 132 may be provided on the automated diagnostic analysis system 100 that is not directly linked to the track 121. For instance, an independent robot 133 (shown dotted) may carry specimen containers 102 containing specimens 212 to the remote station 132 and return them after testing/pre-processing. Optionally, the specimen containers 102 may be manually removed and returned. Remote station 132 may be used to test for certain constituents, such as a hemolysis level, or may be used for further processing, such as to lower a lipemia level through one or more additions and/or through additional processing, or to remove a clot, bubble or foam, for example, that was previously determined by the quality check module 130. Other pre-screening using the HILN detection methods described herein may be accomplished at remote station 132.

Additional station(s) may be provided at one or more locations on or along the track 121. The additional station(s) may include a de-capping station, aliquoting station, one or more additional quality check modules 130, and the like.

The automated diagnostic analysis system 100 may include a number of sensors 116 at one or more locations around the track 121. Sensors 116 may be used to detect a location of specimen containers 102 on the track 121 by means of reading the identification information 218*i*, or like information (not shown) provided on each carrier 122. Any suitable means for tracking the location may be used, such as proximity sensors. All of the sensors 116 may interface with the computer 143, so that the location of each specimen container 102 may be known at all times.

The pre-processing stations and the analyzers 106, 108, and 110 may be equipped with robotic mechanisms and/or inflow lanes configured to remove carriers 122 from the track 121, and with robotic mechanisms and/or outflow lanes configured to reenter carriers 122 to the track 121.

Automated diagnostic analysis system 100 may be controlled by the computer 143, which may be a microprocessor-based central processing unit CPU, having a suitable memory and suitable conditioning electronics and drivers for operating the various system components. Computer 143 may be housed as part of, or separate from, the base 120 of the automated diagnostic analysis system 100. The computer 143 may operate to control movement of the carriers 122 to and from the loading area 105, motion about the track 121, motion to and from the first pre-processing station 125 as well as operation of the first pre-processing station 125 (e.g., centrifuge), motion to and from the quality check module 130 as well as operation of the quality check module 130, and motion to and from each analyzer 106, 108, 110. In some embodiments, the operation of each analyzer 106, 108, 110 for carrying out the various types of testing (e.g., assay or clinical chemistry) can be provided by computer 143, or optionally, each analyzer 106-110 may include its own server or computer, which may interface and communicate with computer 143 via a suitable network, such as a LAN or WAN.

For all but the quality check module 130, the computer 143 may control the automated diagnostic analysis system 100 according to software, firmware, and/or hardware commands or circuits such as those used on the Dimension® clinical chemistry analyzer sold by Siemens Healthcare Diagnostics Inc. of Tarrytown, New York, and such control is typical to those skilled in the art of computer-based electromechanical control programming and will not be further described herein. Other suitable systems for controlling the automated diagnostic analysis system 100 may be used. The control of the quality check module 130 may also be provided by the computer 143, but in accordance with the inventive characterization methods described in detail herein.

The computer 143 as used for image processing and to carry out the characterization methods described herein may include a CPU or GPU, sufficient processing capability and RAM, and suitable storage. In one example, the computer 143 may be a multi-processor-equipped PC with one or more GPUs, 8 GB Ram or more, and a Terabyte or more of storage. In another example, the computer 143 may be a GPU-equipped PC, or optionally a CPU-equipped PC operated in a parallelized mode. A Math Kernel Library (MKL) could be used as well, 8 GB RAM or more, and suitable storage.

Embodiments of the disclosure may be implemented using a computer interface module (CIM) 145 that allows a user to easily and quickly access a variety of control and status display screens of a display 145D. These control and status display screens may display and enable control of some or all aspects of a plurality of interrelated automated devices used for pre-screening, preprocessing preparation, and analysis of specimens 212. The CIM 145 may be employed to provide information about the operational status of a plurality of interrelated automated devices as well as information describing the location of any specimen 212 and a status of tests to be performed on, or being performed on, the specimen 212. The CIM 145 is thus adapted to facilitate interactions between an operator and the automated diagnostic analysis system 100. The display 145D of the CIM 145 may be operative to display a menu including icons, scroll bars, boxes, and buttons through which the operator may interface with the automated diagnostic analysis system 100. The menu may comprise a number of functional elements programmed to display and/or operate functional aspects of the automated diagnostic analysis system 100. As will be apparent from the following, the display 145D may be used to display training images upon which a characterization of a specimen 212 is based.

Figure 4A:
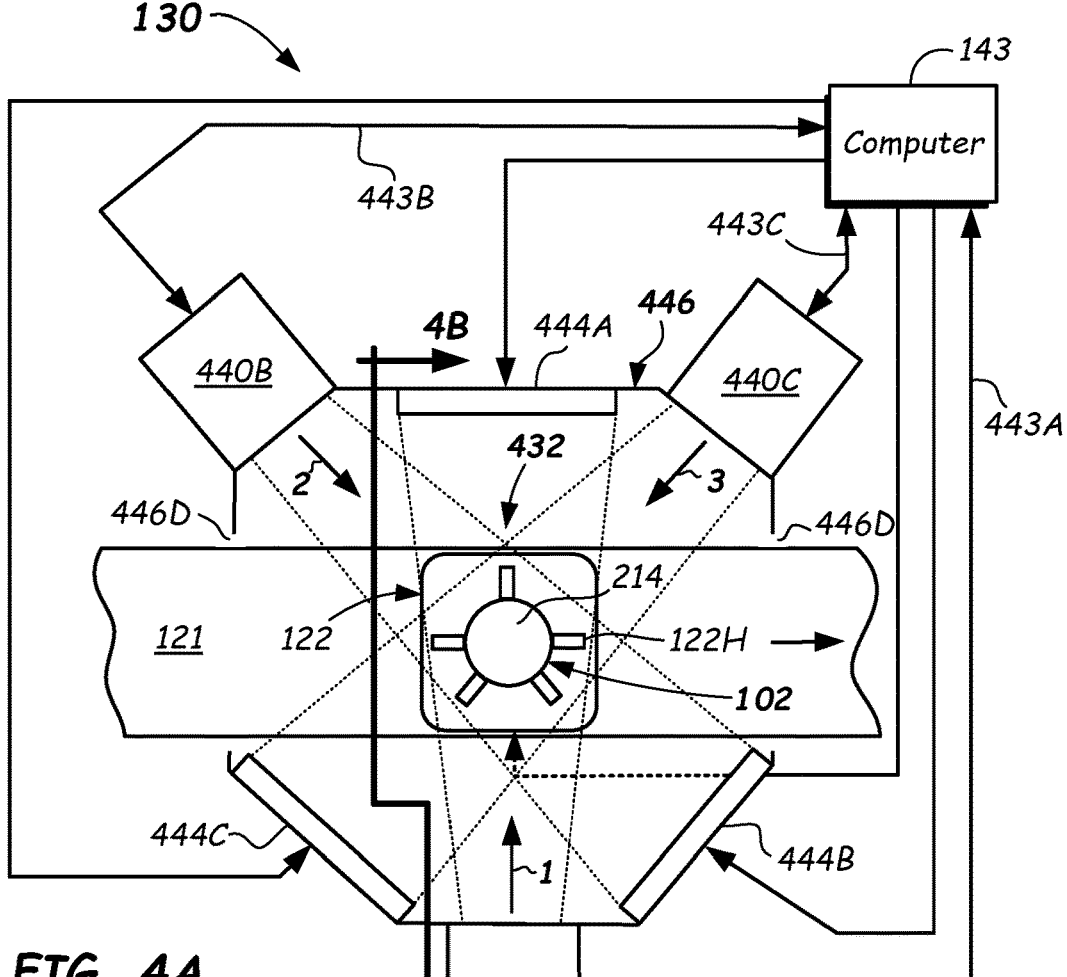
FIG. 4A illustrates a schematic top view of a quality check module (with top removed for illustration purposes) including multiple viewpoints (1, 2, 3) and configured to capture and analyze multiple images to enable pre-screening to determine a presence of an interferent according to one or more embodiments.
Figure 4B:
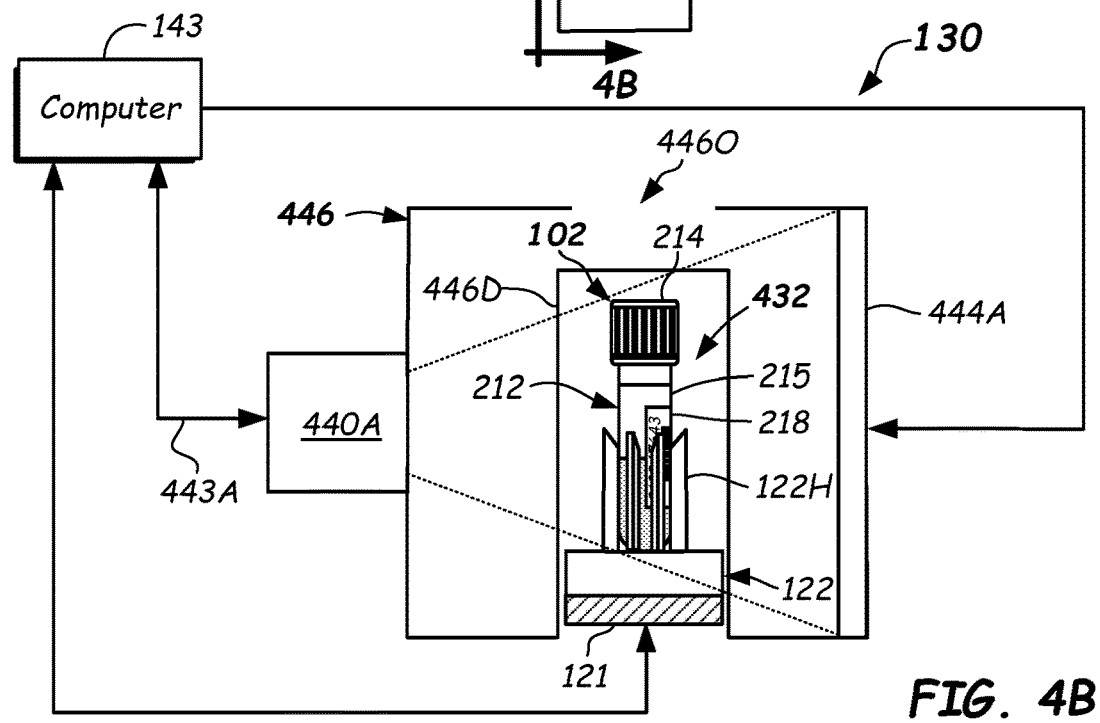
FIG. 4B illustrates a schematic side view of the quality check module (with front enclosure wall removed for illustration purposes) of FIG. 4A taken along section line 4B-4B of FIG. 4A according to one or more embodiments.

FIGS. 4A and 4B show an embodiment of a quality check module 130 configured to carry out the characterization methods as shown and described herein. Quality check module 130 and computer 143 may be configured with programming instructions to pre-screen for a presence and degree of an interferent (e.g., H, I, and/or L) in a specimen 212 (e.g., in a serum or plasma portion 212SP thereof) prior to analysis by the one or more analyzers 106, 108, 110. Pre-screening in this manner allows for additional processing, additional quantification or characterization, and/or discarding and/or redrawing of a specimen 212 without wasting valuable analyzer resources or possibly having the presence of an interferent affect the veracity of the test results.

In addition to the interferent detection methods described herein, other detection methods may take place on the specimen 212 contained in the specimen container 102 at the quality check module 130. For example, a method may be carried out at the quality check module 130 to provide segmentation data. The segmentation data may be used in a post-processing step to quantify the specimen 212, e.g., to determine certain physical dimensional characteristics of the specimen 212, such as LA and SB, and/or determination of HSP, HSB, and/or HTOT. Quantification may also involve estimating, e.g., a volume of the serum or plasma portion (VSP) and/or a volume of the settled blood portion (VSB). Furthermore, the quality check module 130 may be used to quantify geometry of the specimen container 102, i.e., quantify certain physical dimensional characteristics of the specimen container 102, such as the location of TC, HT, and/or W or Wi of the specimen container 102. Other quantifiable geometrical features may also be determined.

Quality check module 130 may include a housing 446 that may at least partially surround or cover the track 121 to minimize outside lighting influences. The specimen container 102 may be located inside the housing 446 during the image-taking sequences. Housing 446 may include one or more doors 446D to allow the carriers 122 to enter into and/or exit from the housing 446. In some embodiments, the ceiling may include an opening 446O to allow a specimen container 102 to be loaded into the carrier 122 by a robot including moveable robot fingers from above.

As shown in FIGS. 4A and 4B, quality check module 130 may include multiple image capture devices 440A-440O configured to capture lateral images of the specimen container 102 and specimen 212 at an imaging location 432 from multiple viewpoints (viewpoints labeled 1, 2, and 3). While three image capture devices 440A-440C are shown and preferred, optionally two, four, or more can be used. As shown, the viewpoints 1-3 may be arranged so that they are approximately equally spaced from one another, such as about 120° from one another. The images may be taken in a round robin fashion, for example, where one or more images from viewpoint 1 may be taken followed sequentially by viewpoints 2 and 3. Other sequences of image taking may be used. Light sources 444A-444C may back light the specimen container 102 (as shown). Multiple viewpoints are advantageous because one or more images taken from viewpoints 1-3 may be partially or fully occluded (i.e., no clear view of the serum or plasma portion 212SP) by one or more labels 218. From the multiple viewpoints at least one un-occluded viewpoint may be found.

As depicted, the image capture devices 440A, 440B, 440C may be arranged around the track 121. Other arrangements of the plurality of image capture devices 440A, 440B, 440C may be used. In this way, the images of the specimen 212 in the specimen container 102 may be taken while the specimen container 102 is residing in the carrier 122 at the imaging location 432. The field of view of the multiple images obtained by the image capture devices 440A, 440B, 440C may overlap slightly in a circumferential extent, when three or more viewpoints are used.

Image capture devices 440A-440O may be any suitable device for capturing well-defined digital images, such as conventional digital cameras capable of capturing a pixelated image, charged coupled devices (CCD), an array of photodetectors, one or more CMOS sensors, or the like. The captured image size may be, e.g., about 2560×694 pixels. In another embodiment, the image capture devices 440A, 440B, 440C may capture an image size that may be about 1280×387 pixels, for example. Other image sizes and pixel densities may be used.

Each image may be triggered and captured at quality check module 130 in response to receiving a triggering signal provided in communication lines 443A, 443B, 443C from the computer 143. Each of the captured images may be processed by the computer 143 according to one or more embodiments. In one particularly effective method, high dynamic range (HDR) processing may be used to capture and process the image data from the captured images.

Figure 5:
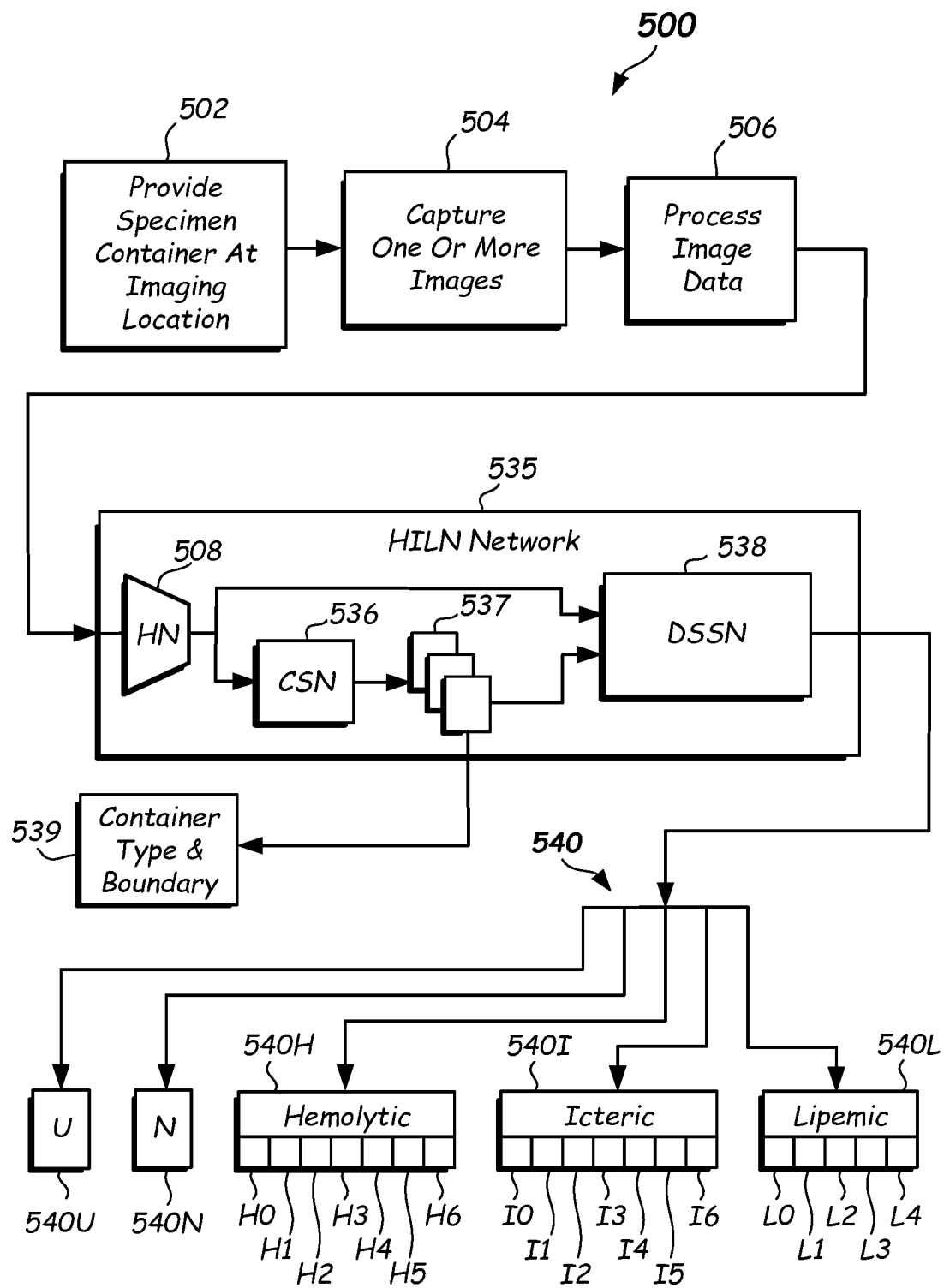
FIG. 5 illustrates a functional block diagram of an HILN network operative to output an interferent determination and classification index of serum or plasma portion of a specimen in a specimen container according to one or more embodiments.

FIG. 5 shows an HILN network architecture 500 configured to carry out the HILN characterization method described herein. Architecture 500 may be implemented in a quality check module 130 controlled by the computer 143 via programming instructions stored in memory. As discussed above, the specimen container 102 may be provided at imaging location 432 (FIGS. 4A and 4B) of the quality check module 130 as represented in functional block 502. One or more images (e.g., multi-viewpoint images) may be captured by the plurality of image capture devices 440A-440O as represented in functional block 504. The image data for each of the multi-viewpoint images may be processed to provide a plurality of optimally-exposed and normalized image data sets (hereinafter "image data sets") as represented in functional block 506 as is described in US Pat. App. Pubs. 2018/0372648 and 2019/0041318 to Wissmann et al. The image data (i.e., pixel data) of an image of a specimen (and specimen container) may be provided as input to an HILN network 535, which may be a segmentation convolutional neural network (SCNN). Other types of HILN networks may be employed to provide an HILN determination.

One task that may take place during pre-processing is the detailed characterization of a specimen container, such as, e.g., specimen container 102. This may include, e.g., separation of the specimen container from its background, understanding of the content and location of the serum or plasma portion 212SP, and segmentation of any labels affixed to the specimen container. All these tasks may be completed with HILN network 535, which can perform pixel-level classification. Given an input image (i.e., pixel data), the HILN network 535 is operative to assign a classification index to each pixel of the image based on its local appearance as indicated by its pixel data value. The extracted pixel index information can be further processed by the HILN network 535 to determine a final HILN classification index. In some embodiments, the classification index may include 21 serum classes, including an un-centrifuged class, a normal class, and 19 HIL classes/subclasses, as described in more detail below.

A challenge to determining an HILN classification index may result from the small appearance differences within each sub-class (index) of the H, I, and L classes. That is, the pixel data values of adjacent sub-classes can be very similar. To overcome these challenges, the HILN network 535 may include a deep semantic segmentation network (DSSN) 538 that includes, in some embodiments, more than 100 operational layers. A deep semantic segmentation network (DSSN) 538 is a deep learning network (also known as deep structured learning) and is part of a broader family of machine learning methods based on artificial neural networks with representation learning. Learning can be supervised, semi-supervised, or unsupervised.

To overcome appearance differences that may be caused by variations in specimen container type (e.g., size and/or shape), the HILN network 535 may also include a container segmentation network (CSN) 536 at the front end of the DSSN 538. The CSN 536 is configured and operative to determine container type and boundary information. The container type and boundary information 537 may be input via an additional input channel to the DSNN 538 and, in some embodiments, the HILN network 535 may provide as an output the determined container type and boundary segmentation 539. In some embodiments, the CSN 536 may have a similar network structure as the DSSN 538, but shallower (i.e., with far fewer layers).

As shown in FIG. 5, an output of the HILN network 535 may be a classification index 540 that, in some embodiments, may include an un-centrifuged class 540U, a normal class 540N, a hemolytic class 540H, an icteric class 540I, and a lipemic class 540L. In some embodiments, hemolytic class 540H may include hemolytic sub-classes H0, H1, H2, H3, H4, H5, and H6. Icteric class 540I may include icteric sub-classes I0, I1, I2, I3, I4, I5, and I6. And lipemic class 540L may include lipemic sub-classes L0, L1, L2, L3, and L4. Each of hemolytic class 540H, icteric class 540I, and/or lipemic class 540L may have, in other embodiments, other numbers of fine-grained sub-classes.

As also shown in FIG. 5, HILN network 535 may include a front-end hashing network 508 (HN) in accordance with one or more embodiments. Front-end hashing network 508 (HN) assigns unique hash codes to the images prior to processing by the DSSN 538. Front-end hashing network 508 (HN) may be configured to operate (via programming instructions) as described below in connection with hashing network 601 of FIG. 6. In alternative embodiments, hashing network 508 may be a back-end hashing network configured to receive from DSSN 538 a segmented region (e.g., a serum or plasma portion 212SP) of an input image of a specimen in a specimen container instead of the full input image itself. A hash code is assigned and indexed to a hash table to allow for ease of later retrieval of the respective training images.

Figure 6:
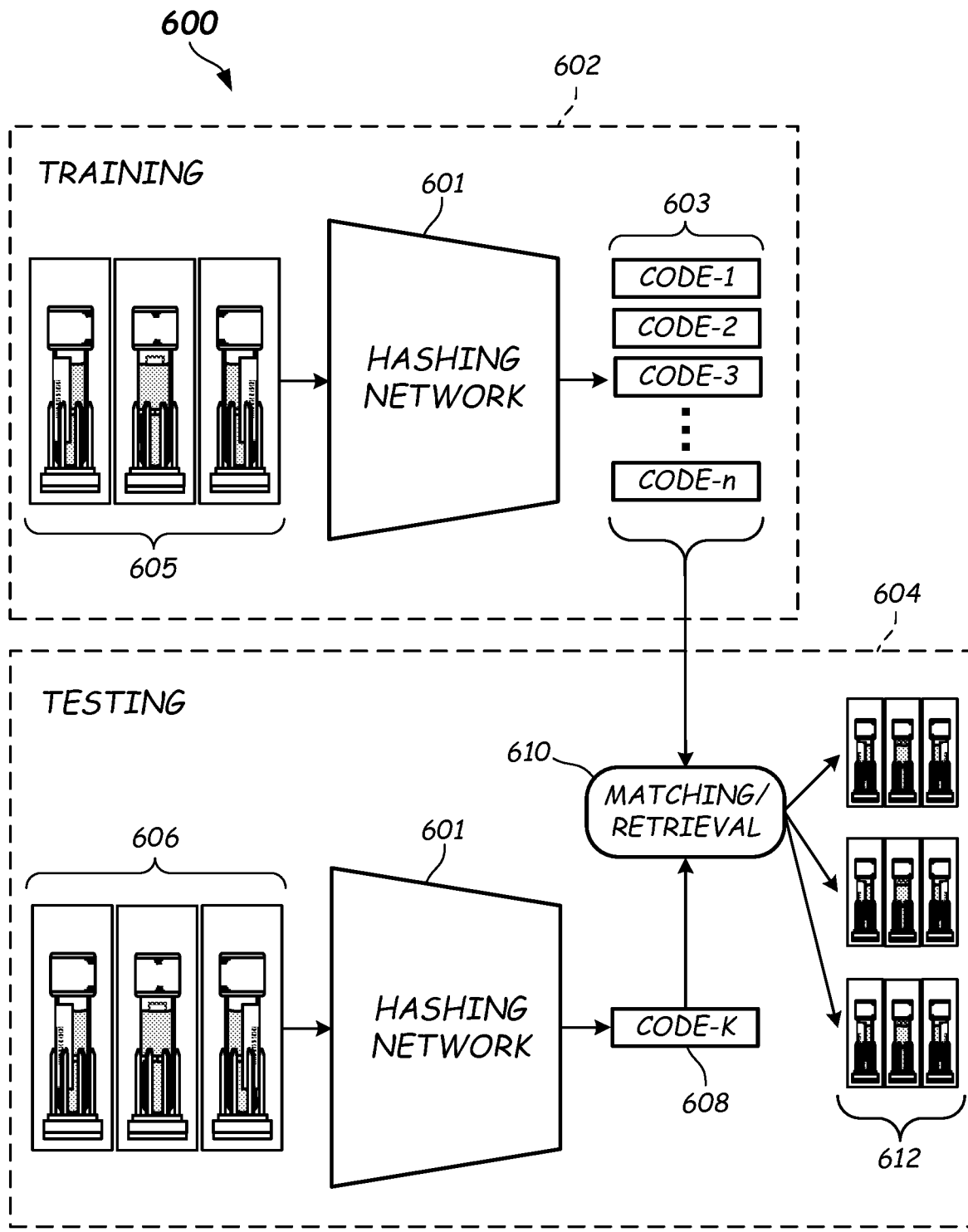
FIG. 6 illustrates a functional block diagram of a hashing network process of the HILN network of FIG. 5 according to one or more embodiments.

FIG. 6 illustrates a hashing network process 600 incorporated within the HILN network 535 of FIG. 5 in accordance with one or more embodiments. Hashing network process 600 includes a hashing network 601, implementable in a training phase 602 and a testing phase 604. During the training phase 602, hashing network 601 provides hashing/indexing for training specimen images 605, wherein such images 605 are used to train HILN network 535, such as DSSN 538, for example. DSSN 538 is trained, for example, to perform at least an HILN determination of a serum or plasma portion 212SP of each sample specimen 212 to be analyzed in the automated diagnostic analysis system 100. Hashing network 601 assigns a unique hash code 603 (e.g., code-1, code-2, code-3, . . . , code-n) to each of the training images or each group of training images 605 representing the same training sample specimen 212. Likewise, hashing network 601 assigns a unique hash code 608 to each test image or group of test images 606. The values returned by a hashing function of the hashing network 601 are known as hash codes. A machine learning algorithm, specifically a hashing neural network is the hashing function producing hash codes. Hash codes are used for indexing the training images 605. For example, the three training images 605 shown in FIG. 6 represent the same sample specimen wherein the three images 605 may have been respectively captured by image capture devices 440A, 440B, 440C from the respective viewpoints 1-3 of FIG. 4A. In some embodiments, hash codes 603 for training images in a similar HILN class index or group may have minimal distance (difference) between them, while hash codes 603 across HILN classes or groups may have large distances between them. The distance between respective hash codes can be determined by any suitable routine, such as a hamming function. The assigned training image hash codes 603 (possibly along with other identifiers of their respective training images) may be stored in a memory, such as in a database of computer 143, and may be later retrieved using a hashing table.

During the testing phase 604, hashing network 601 provides retrieval of specific training images upon which each H1 LN determination is based. As shown in FIG. 6, test specimen images 606 representing viewpoints 1-3 of a same specimen to be analyzed can be input to the hashing network 601, which assigns a unique hash code 608 (code-k) to the test specimen images 606. If the HILN network 535 has been thoroughly trained then the hash code 608 (code-k) assigned may be such that it is minimally distant (e.g., close to or identical with) a specific hash code(s) 603 of the training images that most closely match specimen images 606 as determined by the hashing network 508 or otherwise. For example, a matching/retrieval feature 610 of hashing network process 600 (executed by computer 143) may subsequently retrieve the specific training images 612 upon which the HILN index for the specimen depicted in specimen images 606 is determined, and may present those images to a user via CIM 145, such as on a suitable display screen, for example. The confidence level in the classification can also be displayed.

The closest hash code can be determined by a hamming distance function or other measure of difference between the test sample hashing code 608 and the closest training hashing code 603 for a training image or images 605. The closer the hash codes, the more similar and better match the images have. In some embodiments, the top two or top few training images 605 may be selected as being the closest for display to the user. Once the hash codes are learned, the retrieval technique can be as simple as retrieving the K (K is an integer) nearest neighbors or can be retrieved based on a more advanced retrieval model. K can be set or selectable by a user.

The HILN network 535 can determine that the classification of the test image 606 is incorrect. The incorrect HILN determination and the hashing/indexing and matching/retrieval features of hashing network process 600 advantageously can facilitate debugging of the incorrect HILN determination. This can be accomplished, for example, by providing the basis or reasoning (via retrieved specific training images 612) for each HILN determination made by the HILN network 535. In some embodiments, the incorrect HILN determination is determined based upon a confidence level assigned by the HILN network 535, such as by a Softmax function. For example, if the confidence level is lower than a preselected value, such as 0.75 out of a 0.0 to 1.0 scale, then the HILN determination may be deemed an incorrect HILN determination. In other embodiments, if a distance between the test hash code 608 and the training hash code 603 is greater than a preselected distance, then the HILN determination may be deemed an incorrect HILN determination. Thus, an incorrect HILN determination may flag a comparison of the test image 606 to the specific training images 612 used in the HILN determination by the HILN network 535, and appropriate corrective measures can be undertaken. For example, corrective measures may include retraining of the HILN network 535. Retaining of the HILN network 535 can involve providing a mix of new image data from those images 606 that are deemed to be incorrectly classified and old image data previously used to train the model of the HILN network 535. The training can happen locally or it can be trained on a remote server/cloud. The trained artificial intelligence model can again be tested for verification/validation on the old data that was used for regulatory approval, along with at least some of the newly-collected data from those images 606 that are deemed to be incorrectly classified. The HILN network 535 generates a performance report in compliance with the regulatory process that highlights the improvement over previously trained model. Based on this report, the user can approve the update or the HILN network 535 can be updated automatically. These updates can happen without interrupting the existing workflow. For example, the update can be simply replacing the old model of the HILN network 535 with the new model. This update can be performed by a service technician or it can be remotely downloaded. Thus, the HILN network 535 can be trained with additional training images representing the incorrectly-characterized specimen. Hashing network process 600 also advantageously can identify outliers based on the hash codes, can flexibly add new sets of HILN classes to an HILN network with minimal effort, and provide reports via CIM 145 regarding failure cases (e.g., incorrectly determined HILN indices) and/or specimen samples that need more attention (e.g., more closely-matched training images) via the assigned confidence levels.

Note that in some embodiments, hashing network 601 may be a front-end hashing network, such as the hashing network 508 shown in FIG. 5, a back-end hashing network coupled to receive from DSSN 538 a segmented region of an input image of a specimen and specimen container (operating directly on the segmented regions of the specimen), or a standalone HILN network, incorporating and performing some or all of the functions of CSN 536 and/or DSSN 538 of HILN 535.

Figure 7:
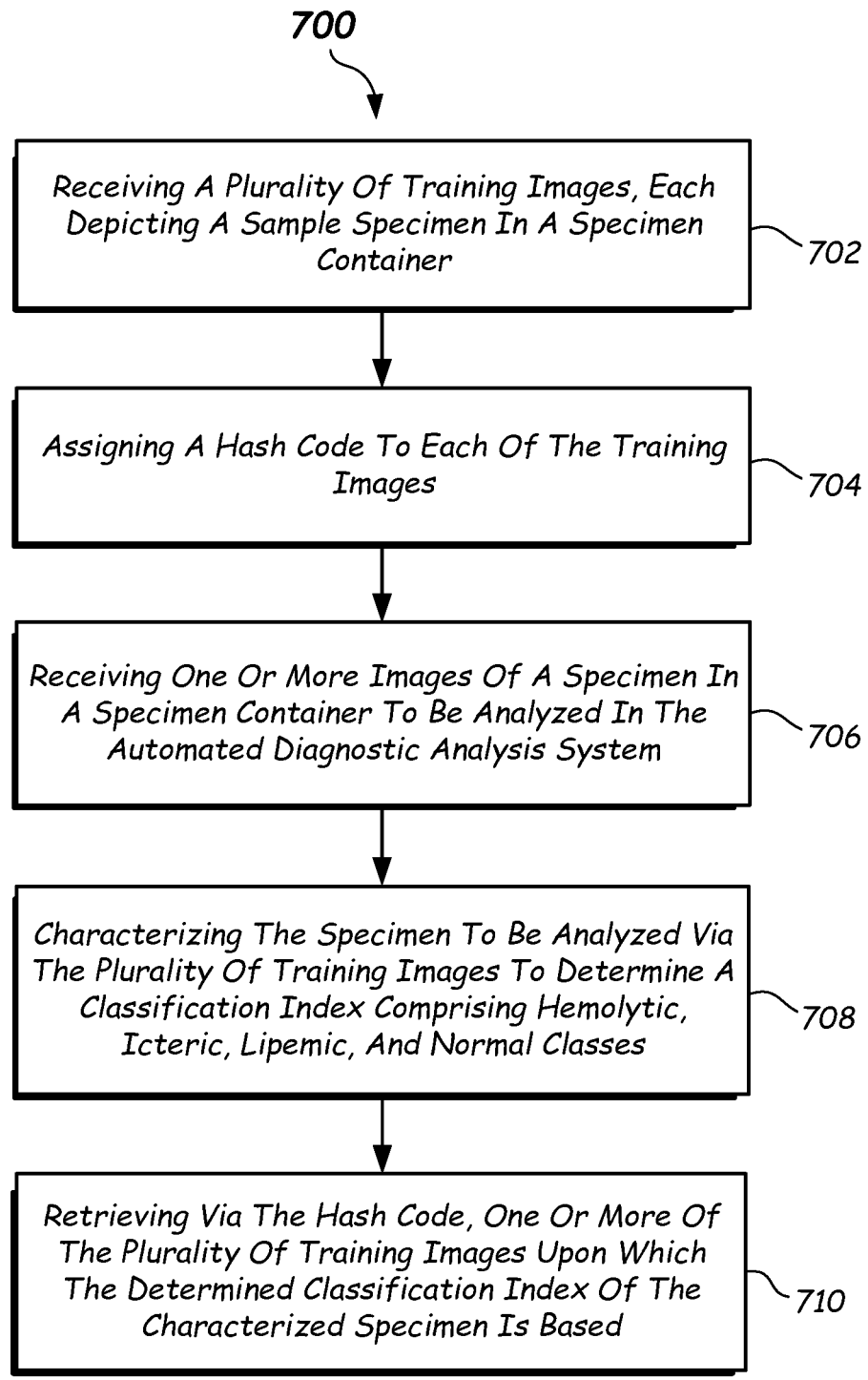
FIG. 7 is flowchart of a method of characterizing a specimen in an automated diagnostic analysis system according to one or more embodiments.

FIG. 7 illustrates a flowchart of a characterization method 700 according to one or more embodiments. The characterization method 700 may be carried out by quality check module 130 (in conjunction with computer 143 and programming instructions) of an automated diagnostic analysis system 100, as described herein, and may include at process block 702, receiving a plurality of training images for training an HILN (hemolytic, icteric, lipemic, normal) network of a quality check module comprising a computer in the automated diagnostic analysis system, each of the training images depicting a sample specimen in a specimen container. The training images may be, e.g., training images 605 of FIG. 6 and/or may be captured by one or more of image capture devices 440A-440O (of FIGS. 4A and 4B) wherein each may be a digital, pixelated image. The training images are used to train an HILN network of a quality check module, such as, e.g., HILN network 535 of quality check module 130.

The characterization method 700 may further include, in process block 704, assigning a hash code to each of the training images via a hashing network of the HILN network. The hash codes may be assigned by hashing network 601 (see FIGS. 5 and 6) and may be, e.g., hash codes 603 of FIG. 6, wherein hash codes for training images 605 in a similar HILN class or group may have minimal distance between them, while hash codes 605 across HILN classes or groups may have large distances between them.

In process block 706, the characterization method 700 may include receiving one or more images of a specimen in a specimen container to be analyzed in the automated diagnostic analysis system. For example, referring to FIGS. 4A and 4B, specimen images may be received from image capture devices 440A, 440B, 440C taken from viewpoints 1-3. The specimen images may be, e.g., specimen images 606 of FIG. 6.

In process block 708, the characterization method 700 may include characterizing the specimen to be analyzed based on the received one or more images via the HILN network using the plurality of training images to determine a classification index comprising hemolytic, icteric, lipemic, and normal classes. For example, the classification index may be classification index 540 (see FIG. 5), which in some embodiments may include the following classes (and subclasses): 540U, 540N, 540H (H0, H1, H2, H3, H4, H5, H6), 540I (I0, I1, I2, I3, I4, I5, I6), and 540L (L0, L1, L2, L3, and L4).

In process block 710, the characterization method 700 may include retrieving via the hash code one or more of the plurality of training images upon which the determined classification index of the characterized specimen is based. For example, referring to FIG. 6, hashing network process 600 may include retrieval feature 610 that may retrieve from a memory of computer 143 (of FIGS. 1, 4A, and 4B) specific training images 612 upon which the HILN determination of specimen images 606 is based.

Accordingly, based on the foregoing it should be apparent that an improved characterization method 700 is provided that facilitates debugging of an incorrect HILN determination.

As should also be apparent, the above characterization methods may be carried out using a quality check module (e.g., quality check module 130), comprising a plurality of image capture devices (e.g., image capture devices) 440A-440C arranged around an imaging location (e.g., imaging location 432), and configured to capture one or more images from one or more viewpoints (e.g., viewpoints 1-3 of FIG. 4A) of a specimen container 102 including one or more labels 218 and containing a specimen 212. The quality check module also includes a computer (e.g., computer 143) coupled to the plurality of image capture devices and configured to process pixel data of the one or more images. The computer (e.g., computer 143) may also be configured and capable of being operated to assign a hash code to each training image via a hashing network, store the assigned hash codes in a memory or database of computer 143, and provide an HILN determination and the specific training images (retrieved via the assigned hash codes) upon which the HILN determination is based.

While the disclosure is susceptible to various modifications and alternative forms, specific method and apparatus embodiments have been shown by way of example in the drawings and are described in detail herein. It should be understood, however, that the particular methods and apparatus disclosed herein are not intended to limit the disclosure but, to the contrary, to cover all modifications, equivalents, and alternatives falling within the scope of the claims.

What is claimed is:

1. A method of characterizing a specimen in an automated diagnostic analysis system, comprising:
receiving a plurality of training images to train an HILN network of a quality check module comprising a computer in the automated diagnostic analysis system, each of the training images depicting a sample specimen in a specimen container; and
assigning a hash code to each of the training images via a hashing network of the HILN network to facilitate retrieval of the one or more of the training images from a computer memory.

2. The method of characterizing a specimen of claim 1, comprising:
receiving one or more images of a specimen in a specimen container to be analyzed in the automated diagnostic analysis system;
characterizing the specimen to be analyzed based on the one or more images via the HILN network using the plurality of training images to determine a classification index comprising hemolytic, icteric, lipemic, or normal classes.

3. The method of characterizing a specimen of claim 2, comprising:
retrieving via the hash code of one or more of the plurality of training images upon which the classification index of the specimen is based.

4. The method of characterizing a specimen of claim 3, wherein the retrieving via the hash code is conditioned on a determination that a classification index of the specimen is incorrect.

5. The method of characterizing a specimen of claim 4, wherein the determination that the classification index of the characterized specimen is incorrect is based upon a confidence level.

6. The method of characterizing a specimen of claim 1, comprising:
comparing one or more images of a specimen in a specimen container with an incorrect HILN determination to the one or more of the plurality of training images upon which the incorrect HILN determination is based.

7. The method of characterizing a specimen of claim 1, wherein the plurality of training images comprise multi-viewpoint images captured by a plurality of image capture devices.

8. The method of characterizing a specimen of claim 1, wherein the HILN network comprises a deep semantic segmentation network (DSSN).

9. The method of characterizing a specimen of claim 1, wherein each of the plurality of training images comprises a classification that comprises one of a hemolytic class, an icteric class, a lipemic class, and a normal class.

10. The method of characterizing a specimen of claim 1, wherein each of the plurality of training images includes a hemolytic sub-class, an icteric sub-class, or a lipemic sub-class.

11. The method of characterizing a specimen of claim 1, wherein the hashing network comprises a front-end hashing network that assigns the hash code prior to segmentation.

12. The method of characterizing a specimen of claim 1, wherein the hashing network comprises a back-end hashing network configured to receive a segmented region of each of the training images and assign the hash code to the segmented region of the specimen.

13. The method of characterizing a specimen of claim 1, wherein assigned training image hash codes are stored in a database of a computer and later retrieved.

14. The method of characterizing a specimen of claim 1, wherein the hashing network assigns the hash code to each group of training images representing a same sample specimen.

15. The method of characterizing a specimen of claim 1, comprising retrieving via the hash code of one or more of the plurality of training images upon which classification of the specimen is based, and presenting the one or more of the plurality of training images to a user on a display screen.

16. The method of characterizing a specimen of claim 1, comprising providing to the HILN network, one or more additional training images representing an incorrectly-characterized specimen.

17. The method of characterizing a specimen of claim 1, wherein the method of characterizing is carried out by the quality check module.

18. The method of characterizing a specimen of claim 1 wherein hash codes for training images in a same HILN class have a first distance between them, while hash codes across HILN classes have larger distances between them.

19. A method of characterizing a specimen, comprising:
receiving a plurality of training images to train an HILN network, each of the training images depicting a sample specimen in a specimen container;
assigning a hash code to each of the training images via a hashing network;
receiving one or more images of a specimen in a specimen container to be analyzed by the HILN network;
characterizing the specimen to be analyzed based on the one or more images via the HILN network using the plurality of training images to determine a classification index of a hemolytic, icteric, lipemic, or normal class; and
retrieving, via the hash code, one or more of the plurality of training images upon which the classification index is based.

20. A quality check module of an automated diagnostic analysis system, comprising:
a plurality of image capture devices arranged around an imaging location and configured to capture multiple images from multiple viewpoints of a specimen container containing a specimen therein; and
a computer coupled to the plurality of image capture devices, the computer configured and operative via programming instructions to:
input a first plurality of images captured by the plurality of image capture devices to an HILN network executing on the computer, the first plurality of images representing a plurality of training images to train the HILN network, each of the training images depicting a sample specimen in a specimen container,
assign a hash code to each of the training images via a hashing network,
input one or more second images captured by the plurality of image capture devices to the HILN network executing on the computer, the one or more second images representing a test specimen in a specimen container to be analyzed in the automated diagnostic analysis system,
characterize the test specimen to be analyzed based on the one or more second images via the HILN network using the plurality of training images to determine a classification index comprising a hemolytic class, icteric class, lipemic class, or normal class, and
retrieve, via the hash code, one or more of the plurality of training images upon which the classification index of the test specimen is based.

* * * * *